(12) United States Patent
Tresch et al.

(10) Patent No.: US 10,508,285 B2
(45) Date of Patent: Dec. 17, 2019

(54) METHOD FOR SCREENING OF GENES CONFERRING INCREASED TOLERANCE TO HERBICIDES

(71) Applicant: BASF SE, Ludwigshafen (DE)

(72) Inventors: Stefan Tresch, Kirchheim (DE); Raphael Aponte, Mannheim (DE); Jens Lerchl, Potsdam ot Golm (DE); Johannes Hutzler, Waldsee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/531,545

(22) PCT Filed: Nov. 20, 2015

(86) PCT No.: PCT/EP2015/077230
§ 371 (c)(1),
(2) Date: May 30, 2017

(87) PCT Pub. No.: WO2016/087234
PCT Pub. Date: Jun. 9, 2016

(65) Prior Publication Data
US 2017/0356003 A1    Dec. 14, 2017

(30) Foreign Application Priority Data
Dec. 1, 2014   (EP) .................................... 14195583

(51) Int. Cl.
*C12N 15/82* (2006.01)
*G01N 21/64* (2006.01)
*A01N 43/00* (2006.01)

(52) U.S. Cl.
CPC ..... *C12N 15/8274* (2013.01); *G01N 21/6486* (2013.01); *A01N 43/00* (2013.01)

(58) Field of Classification Search
None
See application file for complete search history.

(56) References Cited

U.S. PATENT DOCUMENTS

| | | | | |
|---|---|---|---|---|
| 2002/0058249 A1* | 5/2002 | Subramanian | ....... | C12N 9/0004 435/6.13 |
| 2016/0374339 A1* | 12/2016 | Aponte | .................. | C12N 9/001 504/134 |

FOREIGN PATENT DOCUMENTS

| | | |
|---|---|---|
| EP | 242236 A1 | 10/1987 |
| EP | 0293356 | 11/1988 |
| EP | 337899 A1 | 10/1989 |

OTHER PUBLICATIONS

Barbagallo et al, Plant Physiol. Jun. 2003, vol. 132, Issue 2, pp. 485-493 (Year: 2003).*
Kalaji et al, Photosynth Res, Aug. 2014, vol. 122, pp. 121-158 (Year: 2014).*
Belkhodja et al., Chlorophyll Fluorescence as a Possible Tool for Salinity Tolerance Screening in Barley (*Hordeum vulgare* L.), Plant Physiol., 104(2):667-73 (1994).
Bevan, Binary Agrobacterium vectors for plant transformation, Nucleic Acids Res., 12(22):8711-21 (1984).
Christensen et al., Linking Fluorescence Induction Curve and Biomass in Herbicide Screening, Pest Manage. Sci., 59(12):1303-10 (2003).
Dayan et al., Chlorophyll Fluorescence as a Marker for Herbicide Mechanisms of Action, Pesticide Biochemistry and Physiology, 102(3):189-97 (2012).
Demmig-Adams et al. The Role of Xanthophyll Cycle Carotenoids in the Protection of Photosynthesis, Trends in Plant Science, 1(1):21-6 (1996).
Demmig-Adams et al., Carotenoids 3: In Vivo Functions of Carotenoids in Higher Plants, The FASEB Journal, 10(4):403-12 (1996).
Extended European Search Report, European patent application No. 14195583.1, dated Apr. 9, 2015.
Gitelson et al., The Chlorophyll Fluorescence Ratio $F_{735}/F_{700}$ as an Accurate Measure of the Chlorophyll Content in Plants, Remote Sens. Environ., 69(3):296-302 (1999).
Govindjee, Sixty-Three Years Since Kautsky: Chlorophyll A Fluorescence, Au. J. Plant Physiol., 22:131-60 (1995).
Havaux et al., Functioning of Photosystems I and II in Pea Leaves Exposed to Heat Stress in the Presence or Absence of Light, Planta, 186:88-98 (1991).
Höfgen et al., Storage of Competent Cells for Agrobacterium Transformation, Nucleic Acids Res., 16(20):9877 (1988).
International Preliminary Report on Patentability, International Application No. PCT/EP2015/077230, dated Jun. 15, 2017.
International Search Report and Written Opinion, International Application No. PCT/EP2015/077230, dated Jan. 29, 2016.
Kooten et al., The Use of Chlorophyll Fluorescence Nomenclature in Plant Stress Physiology, Photosynthesis Res. 25(3):147-50 (1990).
Kramer et al., Control and Measurement of Photosynthetic Electron Transport in Vivo, pp. 25-66 IN: Baker (ed.), Photosynthesis and the Environment, Kluwer Academic Publishers (1996).
Krause et al., Chlorophyll Fluorescence and Photosynthesis: The Basics, Ann. Rev. Plant Physiol. Plant Molecular Biol., 42:313-349 (1991).
Kwon et al., Enhanced tolerances of transgenic tobacco plants expressing both superoxide dismutase and ascorbate peroxidase in chloroplasts against methyl viologen-mediated oxidative stress, Plant Cell Environ., 25(7):873-82 (2002).
Li et al., Interactive Effects of Drought Stresses and Elevated $CO_2$ Concentration on Photochemistry Efficiency of Cucumber Seedlings, J. Integrative Plant Biol., 50(10):1307-17 (2008).
Linsmaier et al., Organic growth factor requirements of tobacco tissue cultures, Physiologia Plantarium, vol. 18 pp. 100-127 (1965).

(Continued)

*Primary Examiner* — Eileen B O Hara
(74) *Attorney, Agent, or Firm* — Marshall, Gerstein & Borun LLP

(57) ABSTRACT

The present invention relates to a method for identifying a polynucleotide encoding a polypeptide which confers herbicide tolerance to a plant by measuring photosynthetic quantum yield wherein an increase in the electron transport rate of the samples of the transformed plant as compared to the sample of the control plant is indicative for a herbicide tolerance conferring activity of said candidate polypeptide.

8 Claims, 3 Drawing Sheets

Specification includes a Sequence Listing.

(56) References Cited

OTHER PUBLICATIONS

Mahmood et al., Herbicides, Pesticides, and Plant Tolerance: An Overview, pp. 423-448 IN: Ahmad (ed.), Emerging Technologies and Management of Crop Stress Tolerance, vol. 1, Elsevier (2014).
Maxwell et al., Chlorophyll fluorescence—a practical guide, J. Exp. Botany, 51(345):659-68 (2000).
Meng et al., Sink-source transition in tobacco leaves visualized using chlorophyll fluorescence imaging, New Physiologist, 151:585-95 (2001).
Mir et al., Photosynthetic nitrite reduction as influenced by the internal inorganic carbon pool in air-grown cells fo Synechococcus UTEX 625[1], Plant Physiol., 108:313-8 (1995).
Padgette et al., Site-directed mutagenesis of a conserved region of the 5-enolpyruvylshikimate-3-phosphate synthase active site, J. Biol. Chem., 266(33):22364-9 (1991).
Potrykus, Gene Transfer to Plants: assessment of published approaches and results, Annu. Rev. Plant Physiol. Plant Mol. Biol., 42:205-25 (1991).
Schreiber et al., Continuous recording of photochemical and non-photochemical chlorophyll fluorescence quenching with a new type of modulation fluorometer, Photosynthesis Res., 10:51-62 (1986).
Skillman, Quantum Yield Variation Across the Three Pathways of Photosynthesis: Not Yet Out of the Dark, J. Exp. Botany, 59(7):1647-61 (2008).
Voinnet et al., An enhanced transient expression system in plants based on suppression of gene silencing by the p19 protein of tomato bushy stunt virus, The Plant J., 33:949-56 (2003).
Zivcak et al., Application of photosynthetic parameters in the screening of wheat (*Triticum aestivum* L.) genotypes for improved drought and high temperature tolerance, pp. 1247-1250 IN: Allen et al. (eds.), Photosynthesis, Energy from the Sun: 14th International Congress on Photosynthesis, Springer (2008).

* cited by examiner

SEQUENCE LISTING

<160> NUMBER OF SEQ ID NOS: 11

<210> SEQ ID NO 1
<211> LENGTH: 1566
<212> TYPE: DNA
<213> ORGANISM: Zea mays

<400> SEQUENCE: 1

```
atggataagg cttatatcgc tgctctttct gctgctgctt tgttcctcct tcattacctc    60
ttgggtagaa gggctggtgg tgaaggtaag gctaaggcaa agggatctag aagaaggctc   120
cctccatctc ctccagctat tcctttcctt ggacatctcc atctcgtgaa ggctccattc   180
catggtgctc ttgctagact cgctgctaga catggacctg tgttctctat gagactcgga   240
acaagacgtg cagtggtggt gtcatctcct gattgtgcta gagaatgctt caccgagcac   300
gatgtgaact tcgctaacag accactcttc ccatctatga ggctcgcttc attcgatggt   360
gctatgctct ctgtgtcatc ttacggacct tattggagga acctcagaag ggttgcagct   420
gttcagttgc tctctgctca tagagttgga tgcatggctc ctgctatcga ggctcaagtt   480
agagctatgg tgagaaggat ggataggggct gctgcagctg tggtggtgg tgttgctaga   540 gttcaactta agagaaggct tttcgagctt tctctctctg tgctcatgga aactatcgct   600
cacaccaaga cctctagggc tgaagctgat gctgattctg atatgtctac cgaggctcac   660
gagttcaagc agatcgttga tgagcttgtg ccttacatcg gaaccgctaa cagatgggat   720
tacctccctg ttctcagatg gttcgatgtg ttcgagtga ggaacaagat cctcgatgct   780
gtgggaagaa gggatgcttt ccttggaagg cttatcgatg gtgagagacg taggcttgat   840
```

```
gctggtgatg agtctgagtc taagtctatg atcgctgtgc tcctcaccct ccaaaagtct    900
gaacctgagg tgtacaccga taccgtgatc actgctcttt gcgctaacct tttcggagct    960
ggaactgaga ctacttctac tactaccgag tgggctatgt ctttgctcct caaccataga   1020
gaggctctca agaaggctca ggctgagatt gatgctgctg tgggaacttc tagactcgtg   1080
actgctgatg atgtgcctca ccttacttac ctccagtgca tcgtggatga actctcaga    1140
cttcatcctg ctgctcctct tctcttgcct catgaatctg ctgctgattg cactgtggga   1200
ggatacgatg ttcctagagg aactatgctc ctcgtgaacg tgcacgctgt tcatagagat   1260
cctgctgttt ggaggatcc tgatagattc gtgcctgaga gatttgaggg tgctggtgga    1320
aaggctgagg gtagacttct tatgcctttc ggaatgggta agaaagtg ccctggtgag     1380
actctcgctc tcagaactgt tggacttgtt ctcgctactc tcctccagtg cttcgattgg   1440
gatactgtgg atggtgctca agtggatatg aaggcttctg gtggactcac catgcctaga   1500
gctgttcctc ttgaggctat gtgcagacct agaactgcta tgagaggtgt gctcaagaga   1560
ctctga                                                              1566
```

```
<210> SEQ ID NO 2
<211> LENGTH: 521
<212> TYPE: PRT
<213> ORGANISM: Zea mays

<400> SEQUENCE: 2

Met Asp Lys Ala Tyr Ile Ala Ala Leu Ser Ala Ala Ala Leu Phe Leu
1               5                   10                  15

Leu His Tyr Leu Leu Gly Arg Arg Ala Gly Gly Glu Gly Lys Ala Lys
                20                  25                  30

Ala Lys Gly Ser Arg Arg Leu Pro Pro Ser Pro Pro Ala Ile Pro
        35                  40                  45

Phe Leu Gly His Leu His Leu Val Lys Ala Pro Phe His Gly Ala Leu
    50                  55                  60

Ala Arg Leu Ala Ala Arg His Gly Pro Val Phe Ser Met Arg Leu Gly
65                  70                  75                  80

Thr Arg Arg Ala Val Val Val Ser Ser Pro Asp Cys Ala Arg Glu Cys
                85                  90                  95

Phe Thr Glu His Asp Val Asn Phe Ala Asn Arg Pro Leu Phe Pro Ser
            100                 105                 110

Met Arg Leu Ala Ser Phe Asp Gly Ala Met Leu Ser Val Ser Ser Tyr
        115                 120                 125

Gly Pro Tyr Trp Arg Asn Leu Arg Arg Val Ala Ala Val Gln Leu Leu
    130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
            180                 185                 190

Ser Val Leu Met Glu Thr Ile Ala His Thr Lys Thr Ser Arg Ala Glu
        195                 200                 205

Ala Asp Ala Asp Ser Asp Met Ser Thr Glu Ala His Glu Phe Lys Gln
    210                 215                 220

Ile Val Asp Glu Leu Val Pro Tyr Ile Gly Thr Ala Asn Arg Trp Asp
225                 230                 235                 240
```

```
Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
            260                 265                 270

Asp Gly Glu Arg Arg Arg Leu Asp Ala Gly Asp Glu Ser Glu Ser Lys
        275                 280                 285

Ser Met Ile Ala Val Leu Leu Thr Leu Gln Lys Ser Glu Pro Glu Val
    290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
            340                 345                 350

Ala Val Gly Thr Ser Arg Leu Val Thr Ala Asp Asp Val Pro His Leu
        355                 360                 365

Thr Tyr Leu Gln Cys Ile Val Asp Glu Thr Leu Arg Leu His Pro Ala
    370                 375                 380

Ala Pro Leu Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                405                 410                 415

Val His Arg Asp Pro Ala Val Trp Glu Asp Pro Asp Arg Phe Val Pro
            420                 425                 430

Glu Arg Phe Glu Gly Ala Gly Gly Lys Ala Glu Gly Arg Leu Leu Met
        435                 440                 445

Pro Phe Gly Met Gly Arg Arg Lys Cys Pro Gly Glu Thr Leu Ala Leu
    450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                485                 490                 495

Thr Met Pro Arg Ala Val Pro Leu Glu Ala Met Cys Arg Pro Arg Thr
            500                 505                 510

Ala Met Arg Gly Val Leu Lys Arg Leu
        515                 520

<210> SEQ ID NO 3
<211> LENGTH: 2226
<212> TYPE: DNA
<213> ORGANISM: Spinacia oleracea

<400> SEQUENCE: 3
atggctgctt ctagttctct ttctacactc tctcaccacc agaccctctt gtctcatcct      60
aagactcatc tccctactac cccagcttct tctcttctcg tgcctaccac ctcttctaag     120
gttaacggtg tgctcctcaa gtctacctct tcatctagaa ggctcagggt gggatctgct     180
tctgctgttg ttagagctgc tgctgttgag gctctcgagt ctactgatat cgatcagctc     240
gttgagaagt ctgtgaacac catcagattc ctcgctatcg atgctgtgga aaaggctaac     300
tctggacatc ctggactccc tatgggatgt gctcctatgg acatatcct ctacgatgag     360 atcatgaggt acaaccctaa gaaccttac tggttcaaca gggatagatt cgtgctctct     420
gctggacatg gatgtatgct tcagtacgct tccttcacc tcgctggata cgattctgtt     480
ctcgaagagg atctcaagac cttcaggcag tggggatcta gaattcctgg tcaccctgag     540
```

```
aacttcgaga ctcctggtgt tgaggttaca actggacctc ttggacaggg aatcgctaac    600
gctgttggac ttgctcttgc tgagaaacat ctcgctgcta ggttcaacaa gcctgatgct    660
gagatcgtgg atcactacac ctacgtgatc cttggagatg gatgccagat ggaaggtatc    720
gctcaagagg cttgttctct cgctggtcat tggggacttg gaaagcttat cgcttttta    780 gatgataacc acatctctat cgatggtgat accgctatcg ctttcaccga gtctgtggat    840
cttagattcg aggcactcgg atggcatgtg atctgggtta agaacggaaa caccggatat    900
gatgagatta gggctgctat caaagaggct aagaccgtta ccgataagcc taccctcatc    960
aaggtgacca ctactatcgg attcggatct cctaacaagt ctaactcata ctctgtgcac   1020
ggatctgctc tcggatctaa agaggttgag gctaccagac agaacctcgg ttggccttat   1080 gagccttttcc atgttcctga gaggtgaag aagcactggt ctagacatac acctgagggt   1140
gctagtcttg aggctgagtg gaacactaag ttcgctgagt acgagaagaa atacccagag   1200
gatgctaccg agttcaagtc tattaccacc ggtgaattcc ctgctggatg ggagaaggct   1260
ttgcctactt atactcctga cacctggt gatgctacca gaaacttgtc tcagcagtgc    1320
cttaacgctc tcgctaaggt tatccctgga cttcttggtg gatctgctga tctcgcttct   1380
tctaacatga cactcctcaa gatgttcgga gatttcagaa ggacccacag aaagaaagag   1440
actttcaggt tcggagtgag ggaacacgga atgggagcta tctgtaacgg aatctgcctc   1500
cactctcctg gattcgttcc ttactgcgct accttcttcg tgttcaccga ttacatgagg   1560
ggtgctatga ggatctctgc tctttctgag gctggtgtga tctacgtgat gacccacgat   1620
tctatcggac ttggtgagga tggacctact catcaaccta tcgaggctct cagtaagttc   1680
cctgctatgc ctaacatcct catgctcaga cctgctgatg aaacgagac tgctggttct   1740 tacaaggtgg cagtggaaaa cagaaagacc ccttctatcc tcgctctctc taggaagaag   1800
cttcctaacc tccctggaac ctctattgag ggtgttgaga agggaggata cactatcacc   1860
gataactcat ctggaaacaa gccagatgtg atcctcatcg gaaccggatc tgagcttgag   1920
attgctgcta aggctggtga tgagttgagg aaagagggaa aggctgttag ggtggtgtct   1980
ttcgtttctt gggagcttt cgagaagcag tctgatgagt acaaagagtc tgttctcct   2040 tctgatgtga ccgctagagt gtctatcgaa gctggatcta ctttcggttg cacaagatc    2100 gtgggatcta agggtaaggc tatcggaatc gataagttcg gagcttctgc tcctgctggt   2160
aagatctacc aagagtacgg aatcaccgtt gaggctgttg tggaagctgc taagtctgtg   2220
tgttga                                                              2226
```

<210> SEQ ID NO 4  
<211> LENGTH: 741  
<212> TYPE: PRT  
<213> ORGANISM: Spinacia olearcea

<400> SEQUENCE: 4

```
Met Ala Ala Ser Ser Ser Leu Ser Thr Leu Ser His His Gln Thr Leu
1               5                   10                  15

Leu Ser His Pro Lys Thr His Leu Pro Thr Thr Pro Ala Ser Ser Leu
            20                  25                  30

Leu Val Pro Thr Thr Ser Ser Lys Val Asn Gly Val Leu Leu Lys Ser
        35                  40                  45

Thr Ser Ser Ser Arg Arg Leu Arg Val Gly Ser Ala Ser Ala Val Val
    50                  55                  60
```

-continued

Arg Ala Ala Ala Val Glu Ala Leu Glu Ser Thr Asp Ile Asp Gln Leu
65                  70                  75                  80

Val Glu Lys Ser Val Asn Thr Ile Arg Phe Leu Ala Ile Asp Ala Val
            85                  90                  95

Glu Lys Ala Asn Ser Gly His Pro Gly Leu Pro Met Gly Cys Ala Pro
                100                 105                 110

Met Gly His Ile Leu Tyr Asp Glu Ile Met Arg Tyr Asn Pro Lys Asn
            115                 120                 125

Pro Tyr Trp Phe Asn Arg Asp Arg Phe Val Leu Ser Ala Gly His Gly
        130                 135                 140

Cys Met Leu Gln Tyr Ala Leu Leu His Leu Ala Gly Tyr Asp Ser Val
145                 150                 155                 160

Leu Glu Glu Asp Leu Lys Thr Phe Arg Gln Trp Gly Ser Arg Ile Pro
                165                 170                 175

Gly His Pro Glu Asn Phe Glu Thr Pro Gly Val Glu Val Thr Thr Gly
            180                 185                 190

Pro Leu Gly Gln Gly Ile Ala Asn Ala Val Gly Leu Ala Leu Ala Glu
        195                 200                 205

Lys His Leu Ala Ala Arg Phe Asn Lys Pro Asp Ala Glu Ile Val Asp
210                 215                 220

His Tyr Thr Tyr Val Ile Leu Gly Asp Gly Cys Gln Met Glu Gly Ile
225                 230                 235                 240

Ala Gln Glu Ala Cys Ser Leu Ala Gly His Trp Gly Leu Gly Lys Leu
                245                 250                 255

Ile Ala Phe Tyr Asp Asp Asn His Ile Ser Ile Asp Gly Asp Thr Ala
            260                 265                 270

Ile Ala Phe Thr Glu Ser Val Asp Leu Arg Phe Glu Ala Leu Gly Trp
        275                 280                 285

His Val Ile Trp Val Lys Asn Gly Asn Thr Gly Tyr Asp Glu Ile Arg
290                 295                 300

Ala Ala Ile Lys Glu Ala Lys Thr Val Thr Asp Lys Pro Thr Leu Ile
305                 310                 315                 320

Lys Val Thr Thr Thr Ile Gly Phe Gly Ser Pro Asn Lys Ser Asn Ser
                325                 330                 335

Tyr Ser Val His Gly Ser Ala Leu Gly Ser Lys Glu Val Glu Ala Thr
            340                 345                 350

Arg Gln Asn Leu Gly Trp Pro Tyr Glu Pro Phe His Val Pro Glu Glu
        355                 360                 365

Val Lys Lys His Trp Ser Arg His Thr Pro Glu Gly Ala Ser Leu Glu
370                 375                 380

Ala Glu Trp Asn Thr Lys Phe Ala Glu Tyr Glu Lys Lys Tyr Pro Glu
385                 390                 395                 400

Asp Ala Thr Glu Phe Lys Ser Ile Thr Thr Gly Glu Phe Pro Ala Gly
                405                 410                 415

Trp Glu Lys Ala Leu Pro Thr Tyr Thr Pro Glu Thr Pro Gly Asp Ala
            420                 425                 430

Thr Arg Asn Leu Ser Gln Gln Cys Leu Asn Ala Leu Ala Lys Val Ile
        435                 440                 445

Pro Gly Leu Leu Gly Gly Ser Ala Asp Leu Ala Ser Ser Asn Met Thr
450                 455                 460

Leu Leu Lys Met Phe Gly Asp Phe Arg Arg Thr His Arg Lys Lys Glu
465                 470                 475                 480

Thr Phe Arg Phe Gly Val Arg Glu His Gly Met Gly Ala Ile Cys Asn
                485                 490                 495
Gly Ile Cys Leu His Ser Pro Gly Phe Val Pro Tyr Cys Ala Thr Phe
            500                 505                 510
Phe Val Phe Thr Asp Tyr Met Arg Gly Ala Met Arg Ile Ser Ala Leu
        515                 520                 525
Ser Glu Ala Gly Val Ile Tyr Val Met Thr His Asp Ser Ile Gly Leu
    530                 535                 540
Gly Glu Asp Gly Pro Thr His Gln Pro Ile Glu Ala Leu Ser Lys Phe
545                 550                 555                 560
Pro Ala Met Pro Asn Ile Leu Met Leu Arg Pro Ala Asp Gly Asn Glu
                565                 570                 575
Thr Ala Gly Ser Tyr Lys Val Ala Val Glu Asn Arg Lys Thr Pro Ser
            580                 585                 590
Ile Leu Ala Leu Ser Arg Lys Lys Leu Pro Asn Leu Pro Gly Thr Ser
        595                 600                 605
Ile Glu Gly Val Glu Lys Gly Gly Tyr Thr Ile Thr Asp Asn Ser Ser
    610                 615                 620
Gly Asn Lys Pro Asp Val Ile Leu Ile Gly Thr Gly Ser Glu Leu Glu
625                 630                 635                 640
Ile Ala Ala Lys Ala Gly Asp Glu Leu Arg Lys Glu Gly Lys Ala Val
                645                 650                 655
Arg Val Val Ser Phe Val Ser Trp Glu Leu Phe Glu Lys Gln Ser Asp
            660                 665                 670
Glu Tyr Lys Glu Ser Val Leu Pro Ser Asp Val Thr Ala Arg Val Ser
        675                 680                 685
Ile Glu Ala Gly Ser Thr Phe Gly Trp His Lys Ile Val Gly Ser Lys
    690                 695                 700
Gly Lys Ala Ile Gly Ile Asp Lys Phe Gly Ala Ser Ala Pro Ala Gly
705                 710                 715                 720
Lys Ile Tyr Gln Glu Tyr Gly Ile Thr Val Glu Ala Val Val Glu Ala
                725                 730                 735
Ala Lys Ser Val Cys
            740

<210> SEQ ID NO 5
<211> LENGTH: 1605
<212> TYPE: DNA
<213> ORGANISM: Amaranthus tuberculatus

<400> SEQUENCE: 5
atggttattc aatctatcac tcacctcagt cctaacttgg ctttgccttc tccactctct    60
gtgtctacta agaattaccc tgttgctgtg atgggaaaca tctctgaaag agaggaacct   120
acctctgcta agagagttgc tgttgttgga gctggtgttt ctggacttgc tgctgcttat   180
aagctcaagt ctcatggact ttctgtgaca ctttttcgagg ctgattctag agctggtgga   240
aagcttaaga ccgttaagaa ggatggattc atctgggatg agggtgctaa cactatgact   300
gaatctgagg ctgaggtgtc atctcttatc gatgatcttg actcagaga gaagcaacag   360 cttcctatct ctcagaacaa gagatatatc gctagggatg acttcctgt gcttcttcct   420 tctaatcctg ctgctctcct cacttctaac atcctttctg ctaagtctaa gctccagatc   480
atgcttgaac cattccttgg gagaaagcac aacgctactg agcttctga tgagcatgtt   540 caagagtctg tgggagaatt cttcgagaga catttcggaa agaattcgt ggattacgtg   600

```
atcgatcctt tcgttgctgg aacttgtggt ggtgatcctc aatctctctc tatgcatcat    660
actttccctg aggtttggaa catcgagaag agattcggat ctgttttcgc tggacttatc    720
cagtctaccc tcttgtctaa gaaagaaaag ggtggtgaga acgcttctat caagaagcct    780
agagttaggg gatctttctc attccaaggt ggaatgcaga ctctcgttga tacaatgtgt    840
aagcagcttg gagaggatga gcttaagctt cagtgtgagg ttctctcttt gtcttacaac    900
cagaagggaa tcccatctct tggaaactgg tctgtgtcat ctatgtctaa caacacctct    960
gaggatcagt cttacgatgc tgttgttgtt accgctccta tcagaaacgt gaaagaaatg   1020
aagatcatga agtccggaaa ccctttctct ctcgatttca ttcctgaggt tacctacgtt   1080
ccactctcag ttatgatcac cgcttttcaag aaagataagg tgaagaggcc acttgaggga   1140
ttcggagttc ttattccttc taaagagcag cacaacggac ttaagactca aggaactctc   1200
ttctcttcta tgatgttccc tgatagggct ccttctgata tgtgcctttt cactactatg   1260
gtgggaggat ctaggaacag aaagcttgct aacgcttcta ccgatgagtt gaagcagatc   1320
gtttcttctg atcttcagca gcttctcgga actgaagatg aaccttcttt cgtgaaccac   1380
ctcttttggt ctaacgcttt tcctctctac ggacacaact acgattctgt tctcagggct   1440
atcgataaga tggaaaagga tctccctgga ttcttctacg ctggaaatca aagggtggt    1500
ctttctgttg aaaggctat ggcttctgga tgtaaggctg ctgagcttgt tatctcttac   1560
ctcgattctc acatctacgt gaagatggat gagaaaaccg cttga                  1605

<210> SEQ ID NO 6
<211> LENGTH: 534
<212> TYPE: PRT
<213> ORGANISM: Amaranthus tuberculatus

<400> SEQUENCE: 6

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190
```

Gly Lys Glu Phe Val Asp Tyr Val Ile Asp Pro Phe Val Ala Gly Thr
            195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Gln Gly Thr Leu
385                 390                 395                 400

Phe Ser Ser Met Met Phe Pro Asp Arg Ala Pro Ser Asp Met Cys Leu
                405                 410                 415

Phe Thr Thr Met Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530

<210> SEQ ID NO 7
<211> LENGTH: 1605
<212> TYPE: DNA
<213> ORGANISM: Amaranthus tuberculatus

<400> SEQUENCE: 7
atggttattc aatctatcac tcacctcagt cctaacttgg ctttgccttc tccactctct      60
gtgtctacta agaattaccc tgttgctgtg atgggaaaca tctctgaaag agaggaacct     120
acctctgcta agagagttgc tgttgttgga gctggtgttt ctggacttgc tgctgcttat     180

```
aagctcaagt ctcatggact ttctgtgaca ctttcgagg ctgattctag agctggtgga      240
aagcttaaga ccgttaagaa ggatggattc atctgggatg agggtgctaa cactatgact     300
gaatctgagg ctgaggtgtc atctcttatc gatgatcttg gactcagaga gaagcaacag     360
cttcctatct ctcagaacaa gctctatatc gctaggatgg acttcctgt gcttcttcct      420 tctaatcctg ctgctctcct cacttctaac atcctttctg ctaagtctaa gctccagatc     480
atgcttgaac cattcctttg gagaaagcac aacgctactg agctttctga tgagcatgtt     540
caagagtctg tgggagaatt cttcgagaga catttcggaa agaattcgt ggattacgtg      600 atcgatcctt tcgttgctgg aacttgtggt ggtgatcctc aatctctctc tatgcatcat     660
actttccctg aggtttggaa catcgagaag agattcggat ctgttttcgc tggacttatc     720
cagtctaccc tcttgtctaa gaagaaaag ggtggtgaga acgcttctat caagaagcct      780
agagttaggg gatctttctc attccaaggt ggaatgcaga ctctcgttga tacaatgtgt     840
aagcagcttg gagaggatga gcttaagctt cagtgtgagg ttctctcttt gtcttacaac     900
cagaagggaa tcccatctct tggaaactgg tctgtgtcat ctatgtctaa caacacctct     960
gaggatcagt cttacgatgc tgttgttgtt accgctccta tcagaaacgt gaaagaaatg    1020
aagatcatga agttcggaaa ccctttctct ctcgatttca ttcctgaggt tacctacgtt    1080
ccactctcag ttatgatcac cgcttttcaag aaagataagg tgaagaggcc acttgaggga   1140
ttcggagttc ttattccttc taagagcag cacaacggac ttaagactct tggaactctc     1200
ttctcttcta tgatgttccc tgatagggct ccttctgata tgtgcctttt cactactttc    1260
gtgggaggat ctaggaacag aaagcttgct aacgcttcta ccgatgagtt gaagcagatc    1320
gtttcttctg atcttcagca gcttctcgga actgaagatg aaccttcttt cgtgaaccac    1380
ctcttttggt ctaacgcttt tcctctctac ggacacaact acgattctgt tctcagggct    1440
atcgataaga tggaaaagga tctccctgga ttcttctacg ctggaaatca aagggtggt     1500 ctttctgttg gaaaggctat ggcttctgga tgtaaggctg ctgagcttgt tatctcttac    1560
ctcgattctc acatctacgt gaagatggat gagaaaaccg cttga                    1605
```

<210> SEQ ID NO 8
<211> LENGTH: 534
<212> TYPE: PRT
<213> ORGANISM: Amaranthus tuberculatus

<400> SEQUENCE: 8

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Leu
        115                 120                 125
```

```
Tyr Ile Ala Arg Asp Gly Leu Pro Val Leu Leu Pro Ser Asn Pro Ala
130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
                260                 265                 270

Gln Thr Leu Val Asp Thr Met Cys Lys Gln Leu Gly Glu Asp Glu Leu
            275                 280                 285

Lys Leu Gln Cys Glu Val Leu Ser Leu Ser Tyr Asn Gln Lys Gly Ile
        290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
                340                 345                 350

Phe Ile Pro Glu Val Thr Tyr Val Pro Leu Ser Val Met Ile Thr Ala
            355                 360                 365

Phe Lys Lys Asp Lys Val Lys Arg Pro Leu Glu Gly Phe Gly Val Leu
        370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
                420                 425                 430

Ser Thr Asp Glu Leu Lys Gln Ile Val Ser Ser Asp Leu Gln Gln Leu
            435                 440                 445

Leu Gly Thr Glu Asp Glu Pro Ser Phe Val Asn His Leu Phe Trp Ser
        450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
530
```

<210> SEQ ID NO 9
<211> LENGTH: 1644
<212> TYPE: DNA
<213> ORGANISM: Alopecurus myosuroides

<400> SEQUENCE: 9

```
atgcttactt cagctacaac tccttctagt tcttctgctt cttctagggc ttctaccagg      60
ttcgcttctt catcaaggcc tagaaggacc gcttatgcta gaggaagaag gctcagacct     120
gttctcgcta tggctgcttc tgatgatcct agggctagat ctgttgctgt gtgggagct      180
ggaatctctg gacttgttgc tgcttacagg ctctctaagt ctggtgtgag agtgactgtg     240
ttcgaggcta tgatagggc tggtggaaag atcaggacca actctgattc tggattcctc      300
tgggatgagg gtgctaacac tatgactgag tctgctctcg aggcttctag gcttatcgat     360
gatcttggac tcgaggatag gctccagtac cctaactctc agcacaagag atacaccgtg     420
aaggatggtg ctcctgctct cattccttct gatcctatcg ctcttatgaa gtcatcactc     480
ctcagtacca agtctaagtt caagttgttc ctcgagccat tcctctacga taagtcatct     540
accaagagtt ctaagaaagt gtctgatgag cacatctctg agtctgtggg atcattcttc     600
gagaggcact tcgaaaaaga gtggtggat tacctcatcg atcctttcgt ggctggaacc      660
tctgctggtg atcctgagtc tttgtctatc aggcatgctt ccctggact ttggaacctc      720
gagaagaagt acggatctat catcgtggga gctatcatgt ctaagctcac cgctaagggt    780
gataagaagg gatctgctgt ttctggaaag ggtaggaaca gagggcttc tttctcttc      840
cacggtggaa tgcagactct cgtggatgct ctccacaaag aggttggaga tggaaacgtt    900
aagctcggtg ctcaggttct ctctctcgct tgtatctgtg atggactctc tgcttcagat    960
ggatggtcta tctctgtgga ttctaaggat gcttctaaca agagcttac caagaaccac   1020
tctttcgatg ctgtgatcat gaccgctcca ctctcaaacg tgcagaggat gaagtttacc   1080
aagggtggtg cacctttcgt gctcgatttc ttgcctaaag ttgattacct cccactctct   1140
ctcatggtga ccgctttcaa gaagaggat gttaagaggc cactcgaggg attcggagtt    1200
ctcatccctt acaaagagca gcagaagcac ggactcaaga ctctcggaac tctcttctct   1260
tctatgatgt cccagatag gctcctaac gatcagcacc tcttcactac tttcgtggga    1320
ggatctcaca caggggatct tgctggtgct ccaaccagta tccttaagca gctcgtgact   1380
tctgatctcg gaaagcttct ggagttgag gacagccta cctcgtgaa gcacatccat     1440
tggagaaacg ctttccctct ctacggacac gattacgatt ctgctttgga ggctatcgga   1500
aagatggaat ctgatctccc tggattcttc tacgctggaa caacaagga tggactcgct   1560
gtgggtaacg tgatcgcttc tggatctaag accgctgatc tcgtgatctc ttacctcgag   1620
tctggaatca gcaggataa ctga                                          1644
```

<210> SEQ ID NO 10
<211> LENGTH: 547
<212> TYPE: PRT
<213> ORGANISM: Alopecurus myosuroides

<400> SEQUENCE: 10

Met Leu Thr Ser Ala Thr Thr Pro Ser Ser Ser Ala Ser Ser Arg
1               5                   10                  15

Ala Ser Thr Arg Phe Ala Ser Ser Ser Arg Pro Arg Arg Thr Ala Tyr
            20                  25                  30

Ala Arg Gly Arg Arg Leu Arg Pro Val Leu Ala Met Ala Ala Ser Asp
        35                  40                  45

```
Asp Pro Arg Ala Arg Ser Val Ala Val Val Gly Ala Gly Ile Ser Gly
    50                  55                  60

Leu Val Ala Ala Tyr Arg Leu Ser Lys Ser Gly Val Arg Val Thr Val
65                  70                  75                  80

Phe Glu Ala Asp Asp Arg Ala Gly Gly Lys Ile Arg Thr Asn Ser Asp
                85                  90                  95

Ser Gly Phe Leu Trp Asp Glu Gly Ala Asn Thr Met Thr Glu Ser Ala
            100                 105                 110

Leu Glu Ala Ser Arg Leu Ile Asp Asp Leu Gly Leu Glu Asp Arg Leu
        115                 120                 125

Gln Tyr Pro Asn Ser Gln His Lys Arg Tyr Thr Val Lys Asp Gly Ala
    130                 135                 140

Pro Ala Leu Ile Pro Ser Asp Pro Ile Ala Leu Met Lys Ser Ser Leu
145                 150                 155                 160

Leu Ser Thr Lys Ser Lys Phe Lys Leu Phe Leu Glu Pro Phe Leu Tyr
                165                 170                 175

Asp Lys Ser Ser Thr Lys Ser Ser Lys Lys Val Ser Asp Glu His Ile
            180                 185                 190

Ser Glu Ser Val Gly Ser Phe Phe Glu Arg His Phe Gly Lys Glu Val
        195                 200                 205

Val Asp Tyr Leu Ile Asp Pro Phe Val Ala Gly Thr Ser Ala Gly Asp
    210                 215                 220

Pro Glu Ser Leu Ser Ile Arg His Ala Phe Pro Gly Leu Trp Asn Leu
225                 230                 235                 240

Glu Lys Lys Tyr Gly Ser Ile Ile Val Gly Ala Ile Met Ser Lys Leu
                245                 250                 255

Thr Ala Lys Gly Asp Lys Lys Gly Ser Ala Val Ser Gly Lys Gly Arg
            260                 265                 270

Asn Lys Arg Ala Ser Phe Ser Phe His Gly Gly Met Gln Thr Leu Val
        275                 280                 285

Asp Ala Leu His Lys Glu Val Gly Asp Gly Asn Val Lys Leu Gly Ala
    290                 295                 300

Gln Val Leu Ser Leu Ala Cys Ile Cys Asp Gly Leu Ser Ala Ser Asp
305                 310                 315                 320

Gly Trp Ser Ile Ser Val Asp Ser Lys Asp Ala Ser Asn Lys Glu Leu
                325                 330                 335

Thr Lys Asn His Ser Phe Asp Ala Val Ile Met Thr Ala Pro Leu Ser
            340                 345                 350

Asn Val Gln Arg Met Lys Phe Thr Lys Gly Gly Ala Pro Phe Val Leu
        355                 360                 365

Asp Phe Leu Pro Lys Val Asp Tyr Leu Pro Leu Ser Leu Met Val Thr
    370                 375                 380

Ala Phe Lys Lys Glu Asp Val Lys Arg Pro Leu Glu Gly Phe Gly Val
385                 390                 395                 400

Leu Ile Pro Tyr Lys Glu Gln Gln Lys His Gly Leu Lys Thr Leu Gly
                405                 410                 415

Thr Leu Phe Ser Ser Met Met Phe Pro Asp Arg Ala Pro Asn Asp Gln
            420                 425                 430

His Leu Phe Thr Thr Phe Val Gly Gly Ser His Asn Arg Asp Leu Ala
        435                 440                 445

Gly Ala Pro Thr Ser Ile Leu Lys Gln Leu Val Thr Ser Asp Leu Gly
    450                 455                 460
```

```
Lys Leu Leu Gly Val Glu Gly Gln Pro Thr Phe Val Lys His Ile His
465                 470                 475                 480

Trp Arg Asn Ala Phe Pro Leu Tyr Gly His Asp Tyr Asp Ser Ala Leu
                485                 490                 495

Glu Ala Ile Gly Lys Met Glu Ser Asp Leu Pro Gly Phe Phe Tyr Ala
            500                 505                 510

Gly Asn Asn Lys Asp Gly Leu Ala Val Gly Asn Val Ile Ala Ser Gly
        515                 520                 525

Ser Lys Thr Ala Asp Leu Val Ile Ser Tyr Leu Glu Ser Gly Ile Lys
    530                 535                 540

Gln Asp Asn
545

<210> SEQ ID NO 11
<211> LENGTH: 10980
<212> TYPE: DNA
<213> ORGANISM: Artificial
<220> FEATURE:
<223> OTHER INFORMATION: Cloning Vector

<400> SEQUENCE: 11
```

| | | | | | |
|---|---|---|---|---|---|
| gtgattttgt | gccgagctgc | cggtcgggga | gctgttggct | ggctggtggc | aggatatatt | 60 |
| gtggtgtaaa | caaattgacg | cttagacaac | ttaataacac | attgcggacg | tctttaatgt | 120 |
| actgaattta | gttactgatc | actgattaag | tactgatatc | ggtacctttc | tttacgaggt | 180 |
| aattgatctc | gcattatata | tctacatttt | ggttatgtta | cttgacatat | agtcattgat | 240 |
| tcaatagttc | tgttaattcc | tttaaagatc | attttgacta | gaccacattc | ttggttcatt | 300 |
| cctcaataat | ttgtaatcat | attggtggat | atagaagtag | attggttata | gatcagatag | 360 |
| tggaagactt | taggatgaat | ttcagctagt | ttttttttt | ggcttattgt | ctcaaaagat | 420 |
| tagtgctttg | ctgtctccat | tgcttctgct | atcgacacgc | ttctgtctcc | ttgtatcttt | 480 |
| attatatcta | ttcgtcccat | gagttttgtt | tgttctgtat | tcgttcgctc | tggtgtcatg | 540 |
| gatggagtct | ctgttccatg | tttctgtaat | gcatgttggg | ttgtttcatg | caagaaatgc | 600 |
| tgagataaac | actcatttgt | gaaagtttct | aaactctgaa | tcgcgctaca | ggcaatgctc | 660 |
| cgaggagtag | gaggagaaga | acgaaccaaa | cgacattatc | agccctttga | ggaagctctt | 720 |
| agttttgtta | ttgttttgt | agccaaattc | tccattctta | ttccattttc | acttatctct | 780 |
| tgttccttat | agaccttata | agtttttat | tcatgtatac | aaattatatt | gtcatcaaga | 840 |
| agtatctttc | aaatctaaat | ctcaaatcac | caggactatg | tttttgtcca | attcgtggaa | 900 |
| ccaacttgca | gcttgtatcc | attctcttaa | ccaataaaaa | aagaaagaaa | gatcaatttg | 960 |
| ataaattttct | cagccacaaa | ttctacattt | aggttttagc | atatcgaagg | ctcaatcaca | 1020 |
| aatacaatag | atagactaga | gattccagcg | tcacgtgagt | tttatctata | aataaaggac | 1080 |
| caaaaatcaa | atcccgaggg | cattttcgta | atccaacata | aaaccccttaa | acttcaagtc | 1140 |
| tcattttaa | acaaatcatg | ttcacaagtc | tcttcttctt | ctctgtttct | ctatctcttg | 1200 |
| ctcgggccct | tagatctcgt | gccgtcgtgc | gacgttgttt | tccggtacgt | ttattcctgt | 1260 |
| tgattccttc | tctgtctctc | tcgattcact | gctacttctg | tttggattcc | tttcgcgcga | 1320 |
| tctctggatc | cgtgcgttat | tcattggctc | gtcgttttca | gatctgttgc | gtttcttctg | 1380 |
| ttttctgtta | tgagtggatg | cgttttcttg | tgattcgctt | gtttgtaatg | ctggatctgt | 1440 |
| atctgcgtcg | tggaattca | aagtgatagt | agttgatatt | ttttccagat | caggcatgtt | 1500 |
| ctcgtataat | caggtctaat | ggttgatgat | tctgcggaat | tatagatcta | agatcttgat | 1560 |

-continued

```
tgatttagat ttgaggatat gaatgagatt cgtaggtcca caaaggtctt gttatctctg    1620
ctgctagata gatgattatc caattgcgtt tcgtagttat ttttatggat tcaaggaatt    1680
gcgtgtaatt gagagtttta ctctgttttg tgaacaggct tgatcaaact cgagatcttt    1740
ctcctgaacc atggcggcgg caacaacaac aacaacaaca tcttcttcga tctccttctc    1800
caccaaacca tctccttcct cctccaaatc accattacca atctccagat tctccctccc    1860
attctcccta acccccaaca aatcatcctc ctcctcccgc cgccgcggta tcaaatccag    1920
ctctccctcc tccatctccg ccgtgctcaa cacaaccacc aatgtcacaa ccactccctc    1980
tccaaccaaa cctaccaaac ccgaaacatt catctcccga ttcgctccag atcaaccccg    2040
caaaggcgct gatatcctcg tcgaagcttt agaacgtcaa ggcgtagaaa ccgtattcgc    2100
ttaccctgga ggtacatcaa tggagattca ccaagcctta acccgctctt cctcaatccg    2160
taacgtcctt cctcgtcacg aacaaggagg tgtattcgca gcagaaggat acgctcgatc    2220
ctcaggtaaa ccaggtatct gtatagccac ttcaggtccc ggagctacaa atctcgttag    2280
cggattagcc gatgcgttgt tagatagtgt tcctcttgta gcaatcacag acaagtccc    2340 tcgtcgtatg attggtacag atgcgtttca agagactccg attgttgagg taacgcgttc    2400
gattacgaag cataactatc ttgtgatgga tgttgaagat atccctagga ttattgagga    2460
agctttcttt ttagctactt ctggtagacc tggacctgtt ttggttgatg ttcctaaaga    2520
tattcaacaa cagcttgcga ttcctaattg gaacaggct atgagattac ctggttatat    2580
gtctaggatg cctaaacctc cggaagattc tcatttggag cagattgtta ggttgatttc    2640
tgagtctaag aagcctgtgt tgtatgttgg tggtggttgt ttgaattcta gcgatgaatt    2700
gggtaggttt gttgagctta cggggatccc tgttgcgagt acgttgatgg ggctgggatc    2760
ttatccttgt gatgatgagt tgtcgttaca tatgcttgga atgcatggga ctgtgtatgc    2820
aaattacgct gtggagcata gtgatttgtt gttggcgttt ggggtaaggt ttgatgatcg    2880
tgtcacgggg aagcttgagg cttttgctag tagggctaag attgttcata ttgatattga    2940
ctcggctgag attgggaaga ataagactcc tcatgtgtct gtgtgtggtg atgttaagct    3000
ggctttgcaa gggatgaata aggttcttga gaaccgagcg gaggagctta agcttgattt    3060
tggagtttgg aggaatgagt tgaacgtaca gaaacagaag tttccgttga gctttaagac    3120
gtttggggaa gctattcctc cacagtatgc gattaaggtc cttgatgagt tgactgatgg    3180
aaaagccata ataagtactg gtgtcgggca acatcaaatg tgggcggcgc agttctacaa    3240
ttacaagaaa ccaaggcagt ggctatcatc aggaggcctt ggagctatgg gatttggact    3300
tcctgctgcg attggagcgt ctgttgctaa ccctgatgcg atagttgtgg atattgacgg    3360
agatggaagc tttataatga atgtgcaaga gctagccact attcgtgtag agaatcttcc    3420
agtgaaggta ctttttattaa acaaccagca tcttggcatg gttatgcaat gggaagatcg    3480
gttctacaaa gctaaccgag ctcacacatt tctcggggat ccggctcagg aggacgagat    3540
attcccgaac atgttgctgt ttgcagcagc ttgcgggatt ccagcggcga gggtgacaaa    3600
gaaagcagat ctccgagaag ctattcagac aatgctggat acaccaggac cttacctgtt    3660
ggatgtgatt tgtccgcacc aagaacatgt gttgccgatg atcccgaatg gtggcacttt    3720
caacgatgtc ataacggaag gagatggccg gattaaatac tgagagatga aaccggtgat    3780
tatcagaacc ttttatggtc tttgtatgca tatggtaaaa aaacttagtt tgcaatttcc    3840
tgtttgtttt ggtaatttga gttctttta gttgttgatc tgcctgcttt ttggtttacg    3900
tcagactact actgctgttg ttgtttggtt tccttctttt cattttataa ataaataatc    3960
```

-continued

```
cggttcggtt tactccttgt gactggctca gtttggttat tgcgaaatgc gaatggtaaa    4020
ttgagtaatt gaaattcgtt attagggttc taagctgttt taacagtcac tgggttaata    4080
tctctcgaat cttgcatgga aaatgctctt accattggtt tttaattgaa atgtgctcat    4140
atgggccgtg gtttccaaat taaataaaac tacgatgtca tcgagaagta aaatcaactg    4200
tgtccacatt atcagttttg tgtatacgat gaaatagggt aattcaaaat ctagcttgat    4260
atgccttttg gttcatttta accttctgta aacattttt cagattttga acaagtaaat     4320
ccaaaaaaaa aaaaaaaaa tctcaactca acactaaatt attttaatgt ataaaagatg     4380
cttaaaacat ttggcttaaa agaaagaagc taaaaacata gagaactctt gtaaattgaa    4440
gtatgaaaat atactgaatt gggtattata tgaattttc tgatttagga ttcacatgat     4500
ccaaaaagga aatccagaag cactaatcag acattggaag taggaatatt tcaaaaagtt    4560 ttttttttt aagtaagtga caaaagcttt taaaaaatag aaaagaaact agtattaaag     4620
ttgtaaattt aataaacaaa agaaattttt tatatttttt catttctttt tccagcatga    4680
ggttatgatg gcaggatgtg gatttcattt ttttccttt gatagccttt taattgatct     4740
attataattg acgaaaaaat attagttaat tatagatata ttttaggtag tattagcaat    4800
ttacacttcc aaaagactat gtaagttgta aatatgatgc gttgatctct tcatcattca    4860
atggttagtc aaaaaaataa aagcttaact agtaaactaa agtagtcaaa aattgtactt    4920
tagtttaaaa tattacatga ataatccaaa acgacttta tgtgaaacaa aaacaatatc     4980
tagtacgcgt caattgattt aaatttaatt aaaattcgaa tccaaaaatt acggatatga    5040
atataggcat atccgtatcc gaattatccg tttgacagct agcaacgatt gtacaattgc    5100
ttctttaaaa aaggaagaaa gaaagaaaga aaagaatcaa catcagcgtt aacaaacggc    5160
cccgttacgg cccaaacggt catatagagt aacggcgtta agcgttgaaa gactcctatc    5220
gaaatacgta accgcaaacg tgtcatagtc agatcccctc ttccttcacc gcctcaaaca    5280
caaaaataat cttctacagc ctatatatac aacccccct tctatctctc ctttctcaca     5340
attcatcatc tttctttctc tacccccaat tttaagaaat cctctcttct cctcttcatt    5400
ttcaaggtaa atctctctct ctctctctct ctctgttatt ccttgtttta attaggtatg    5460
tattattgct agtttgttaa tctgcttatc ttatgtatgc cttatgtgaa tatctttatc    5520
ttgttcatct catccgttta gaagctataa atttgttgat ttgactgtgt atctacacgt    5580
ggttatgttt atatctaatc agatatgaat ttcttcatat tgttgcgttt gtgtgtacca    5640
atccgaaatc gttgattttt ttcatttaat cgtgtagcta attgtacgta tacatatgga    5700
tctacgtatc aattgttcat ctgtttgtgt ttgtatgtat acagatctga aaacatcact    5760
tctctcatct gattgtgttg ttacatacat agatatagat ctgttatatc atttttttta    5820
ttaattgtgt atatatatat gtgcatagat ctggattaca tgattgtgat tatttacatg    5880
attttgttat ttacgtatgt atatatgtag atctggactt tttggagttg ttgacttgat    5940
tgtatttgtg tgtgtatatg tgtgttctga tcttgatatg ttatgtatgt gcagggcgcg    6000
ccagatctgc ggccgcctgc aggcctagga tcgttcaaac atttggcaat aaagtttctt    6060
aagattgaat cctgttgccg gtcttgcgat gattatcata taatttctgt tgaattacgt    6120
taagcatgta ataattaaca tgtaatgcat gacgttattt atgagatggg tttttatgat    6180
tagagtcccg caattataca tttaatacgc gatagaaaac aaaatatagc gcgcaaacta    6240
ggataaatta tcgcgcgcgg tgtcatctat gttactagat cggccggccg tttaaactta    6300
gttactaatc agtgatcaga ttgtcgtttc ccgccttcac tttaaactat cagtgtttga    6360
```

```
caggatatat tggcgggtaa acctaagaga aaagagcgtt tattagaata atcggatatt    6420
taaaagggcg tgaaaaggtt tatccgttcg tccatttgta tgtcaatatt ggggggggggg   6480
gaaagccacg ttgtgtctca aaatctctga tgttacattg cacaagataa aaatatatca    6540
tcatgaacaa taaaactgtc tgcttacata aacagtaata caagggggtgt tcgccaccat   6600
gagccatatc cagcgtgaaa cctcgtgctc ccgcccgcgc ctcaattcca atatggatgc    6660
cgacctttat ggctacaagt gggcgcgcga caacgtcggc cagtcgggcg cgaccattta    6720
tcggctttat ggcaaacccg atgccccgga actgttcctg aagcacggca aaggcagcgt    6780
cgcaaacgat gtcaccgatg agatggtccg cctgaactgg cttaccgagt tcatgccgct    6840
gccgacgatt aagcatttca tccgtacccc ggacgatgcc tggctcttga ccacggccat    6900
tccgggcaaa acggcctttc aggtccttga agagtacccg gactccggtg agaatatcgt    6960
ggacgccctc gcggtcttcc tccgccgttt gcatagcatc cccgtgtgca actgcccctt    7020
caactcggac cgggttttcc gcctggcaca ggcccagtcg cgcatgaata acggcctcgt    7080
tgacgcgagc gatttcgacg atgaacggaa tggctggccg gtggaacagg tttggaagga    7140
aatgcacaaa ctgcttccgt tctcgccgga ttcggtggtc acgcatggtg attttttccct   7200
ggataatctg atctttgacg agggcaagct gatcggctgc atcgacgtgg gtcgcgtcgg    7260
tatcgccgac cgctatcagg acctggcgat cttgtggaat tgcctcggcg agttctcgcc    7320
ctcgctccag aagcgcctgt tccagaagta cggcatcgac aacccggata tgaacaagct    7380
ccagttccac ctcatgctgg acgaattttt ttgaacagaa ttggttaatt ggttgtaaca    7440
ctggcagagc attacgctga cttgacggga cggcggcttt gttgaataaa tcgaactttt    7500
gctgagttga aggatcgatg agttgaagga ccccgtagaa aagatcaaag gatcttcttg    7560
agatccttttt tttctgcgcg taatctgctg cttgcaaaca aaaaaaccac cgctaccagc    7620
ggtggtttgt ttgccggatc aagagctacc aactcttttt ccgaaggtaa ctggcttcag    7680
cagagcgcag ataccaaata ctgtccttct agtgtagccg tagttaggcc accacttcaa    7740
gaactctgta gcaccgccta catacctcgc tctgctaatc ctgttaccag tggctgctgc    7800
cagtggcgat aagtcgtgtc ttaccgggtt ggactcaaga cgatagttac cggataaggc    7860
gcagcggtcg ggctgaacgg ggggttcgtg cacacagccc agcttggagc gaacgaccta    7920
caccgaactg agatacctac agcgtgagct atgagaaagc gccacgcttc ccgaagggag    7980
aaaggcggac aggtatccgg taagcggcag ggtcggaaca ggagagcgca cgagggagct    8040
tccaggggga aacgcctggt atctttatag tcctgtcggg tttcgccacc tctgacttga    8100
gcgtcgattt ttgtgatgct cgtcaggggg cggagcctat ggaaaaacg ccagcaacgc     8160
ggccttttta cggttcctgg cctttttgctg ccttttgct cacatgttct ttcctgcgtt    8220
atcccctgat tctgtggata accgtattac cgcctttgag tgagctgata ccgctcgccg    8280
cagccgaacg accgagcgca gcgagtcagt gagcgaggaa gcggaagagc gcctgatgcg    8340
gtatttctc cttacgcatc tgtgcggtat ttcacaccgc ataggccgcg ataggccgac     8400
gcgaagcggc gggcgtagg gagcgcagcg accgaagggt aggcgctttt tgcagctctt    8460
cggctgtgcg ctggccagac agttatgcac aggccaggcg ggttttaaga gttttaataa    8520
gttttaaaga gttttaggcg gaaaaatcgc ctttttctc ttttatatca gtcacttaca     8580
tgtgtgaccg gttcccaatg tacgctttg ggttcccaat gtacgggttc cggttcccaa     8640
tgtacggctt tgggttccca atgtacgtgc tatccacagg aaagagacct ttcgacctt     8700
```

-continued

| | |
|---|---|
| tttccccctgc tagggcaatt tgccctagca tctgctccgt acattaggaa ccggcggatg | 8760 |
| cttcgccctc gatcaggttg cggtagcgca tgactaggat cgggccagcc tgccccgcct | 8820 |
| cctccttcaa atcgtactcc ggcaggtcat ttgacccgat cagcttgcgc acggtgaaac | 8880 |
| agaacttctt gaactctccg gcgctgccac tgcgttcgta gatcgtcttg aacaaccatc | 8940 |
| tggcttctgc cttgcctgcg gcgcggcgtg ccaggcggta gagaaaacgg ccgatgccgg | 9000 |
| ggtcgatcaa aaagtaatcg gggtgaaccg tcagcacgtc cgggttcttg ccttctgtga | 9060 |
| tctcgcggta catccaatca gcaagctcga tctcgatgta ctccggccgc ccggtttcgc | 9120 |
| tctttacgat cttgtagcgg ctaatcaagg cttcaccctc ggataccgtc accaggcggc | 9180 |
| cgttcttggc cttcttggta cgctgcatgg caacgtgcgt ggtgtttaac cgaatgcagg | 9240 |
| tttctaccag gtcgtctttc tgctttccgc catcggctcg ccggcagaac ttgagtacgt | 9300 |
| ccgcaacgtg tggacggaac acgcggccgg gcttgtctcc cttcccttcc cggtatcggt | 9360 |
| tcatggattc ggttagatgg gaaaccgcca tcagtaccag gtcgtaatcc cacacactgg | 9420 |
| ccatgccggc ggggcctgcg gaaacctcta cgtgcccgtc tggaagctcg tagcggatca | 9480 |
| cctcgccagc tcgtcggtca cgcttcgaca gacggaaaac ggccacgtcc atgatgctgc | 9540 |
| gactatcgcg ggtgcccacg tcatagagca tcggaacgaa aaaatctggt tgctcgtcgc | 9600 |
| ccttgggcgg cttcctaatc gacggcgcac cggctgccgg cggttgccgg gattctttgc | 9660 |
| ggattcgatc agcggcccct tgccacgatt caccggggcg tgcttctgcc tcgatgcgtt | 9720 |
| gccgctgggc ggcctgcgcg gccttcaact tctccaccag gtcatcaccc agcgccgcgc | 9780 |
| cgatttgtac cgggccggat ggtttgcgac cgctcacgcc gattcctcgg gcttgggggt | 9840 |
| tccagtgcca ttgcagggcc ggcagacaac ccagccgctt acgcctggcc aaccgcccgt | 9900 |
| tcctccacac atggggcatt ccacggcgtc ggtgcctggt tgttcttgat tttccatgcc | 9960 |
| gcctccttta gccgctaaaa ttcatctact catttattca tttgctcatt tactctggta | 10020 |
| gctgcgcgat gtattcagat agcagctcgg taatggtctt gccttggcgt accgcgtaca | 10080 |
| tcttcagctt ggtgtgatcc tccgccggca actgaaagtt gacccgcttc atggctggcg | 10140 |
| tgtctgccag gctggccaac gttgcagcct tgctgctgcg tgcgctcgga cggccggcac | 10200 |
| ttagcgtgtt tgtgcttttg ctcatttttct ctttacctca ttaactcaaa tgagttttga | 10260 |
| tttaatttca gcggccagcg cctggacctc gcgggcagcg tcgccctcgg ttctgattc | 10320 |
| aagaacggtt gtgccggcgg cggcagtgcc tgggtagctc acgcgctgcg tgatacggga | 10380 |
| ctcaagaatg ggcagctcgt accggccag cgcctcggca acctcaccgc cgatgcgcgt | 10440 |
| gcctttgatc gcccgcgaca cgacaaaggc cgcttgtagc cttccatccg tgacctcaat | 10500 |
| gcgctgctta accagctcca ccaggtcggc ggtggcccaa atgtcgtaag ggcttggctg | 10560 |
| caccggaatc agcacgaagt cggctgcctt gatcgcggac acagccaagt ccgccgcctg | 10620 |
| gggcgctccg tcgatcacta cgaagtcgcg ccggccgatg gccttcacgt cgcggtcaat | 10680 |
| cgtcgggcgg tcgatgccga caacggttag cggttgatct tcccgcacgg ccgcccaatc | 10740 |
| gcgggcactg ccctggggat cggaatcgac taacagaaca tcggcccggg cgagttgcag | 10800 |
| ggcgcgggct agatgggttg cgatggtcgt cttgcctgac ccgcctttct ggttaagtac | 10860 |
| agcgataacc ttcatgcgtt cccccttgcgt atttgtttat ttactcatcg catcatatac | 10920 |
| gcagcgaccg catgacgcaa gctgttttac tcaaatacac atcaccttt tagatgatca | 10980 |

METHOD FOR SCREENING OF GENES CONFERRING INCREASED TOLERANCE TO HERBICIDES

CROSS-REFERENCE TO RELATED APPLICATIONS

This application is a U.S. National Stage application of International Patent Application No. PCT/EP2015/077230, filed Nov. 20, 2015, which claims priority to European Patent Application No. 14195583.1, filed Dec. 1, 2014.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "76899_Seqlisting.txt", which was created on May 9, 2017 and is 51,405 bytes in size. The subject matter of the Sequence Listing is incorporated herein in its entirety by reference.

FIELD OF THE INVENTION

The present invention relates to a method for identifying a polynucleotide encoding a polypeptide which confers to a plant resistance or tolerance to herbicides by using fluorescence detection, in particular chlorophyll fluorescence.

BACKGROUND OF THE INVENTION

The herbicide research strategy targets to develop new herbicide tolerant crop (HTC) traits. Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor.

However, identifying new target enzymes which confer herbicide tolerance to a plant when over-expressed and/or mutated is often time consuming due to the long regeneration period of plants upon genetic manipulation and exposure to the test herbicide. The problem of the present invention, thus, resides in the provision of a rapid assay by means of which a selection of polynucleotides can be rapidly screened for their capacity or efficiency to confer herbicide tolerance in plants. The inventors of the present invention have solved this problem by combining the transient expression of candidate genes in plant cells with an assay for measuring chlorophyll fluorescence of plant cells that have been subjected to a certain stress condition, i.e. treatment of the cells with an herbicidal compound.

Chlorophyll fluorescence is light reemitted after being absorbed by chlorophyll molecules of plant leaves. Light energy that has been absorbed by a leaf will excite electrons in chlorophyll molecules. Energy in photosystem II can be converted to chemical energy to drive photosynthesis (photochemistry). If photochemistry is inefficient, excess energy can damage the leaf. Energy can be emitted (known as energy quenching) in the form of heat (called non-photochemical quenching NPQ) or emitted as chlorophyll fluorescence. These three processes are in competition, so fluorescence yield is high when less energy is emitted as heat or used in photochemistry. Therefore, by measuring the amount of chlorophyll fluorescence, the efficiency of photochemistry and non-photochemical quenching can be assessed. The fluorescence emitted from a leaf has a longer wavelength than the light absorbed by the leaf. Therefore, fluorescence can be measured by shining a defined wavelength of light onto a leaf and measuring the level of light emitted at longer wavelengths. According to Gitelson et al., the ratio between chlorophyll fluorescence at 735 nm and the wavelength range 700 nm to 710 nm, F735/F700 could be used as a precise indicator of chlorophyll content in plant leaves [Gitelson, et al (1999). *Remote Sensing of Environment* 69 (3): page 296]. Fluorescence is induced by direct excitation of chlorophyll molecules of photosystem II (PSII) by light and their immediate relaxation. The chloroplast fluorescence results from the reactions of deexcitation of excited chlorophyll molecules. Under ideal conditions, most of the energy from excited molecules is trapped into chemical energy which reduces the fluorescence yield often designated as chlorophyll fluorescence quenching. The amount and degree of variable fluorescence is a measure of chloroplast activity (Mir, N. A., et al., Plant Physiol 108:313-318 (1995)). When PSII is functioning poorly, fluorescence characteristics are altered. Stress exposures such as chilling injury (van Kooten, O., and Snell, Photosyn. Res. 25:147-150 (1990)) and high temperature stress (Havaux, M., et al., Planta 186:88-89 (1991)) can be detected as a reduction in PSII function.

Li et al., 2008, (*J. Integr. Plant Biol.* doi: 10.1111/j.1744-7909.2008.00686.x) reported that chlorophyll a fluorescence imaging system has become ubiquitous in plant ecophysiology studies (Maxwell and Johnson 2000, *J. Exp. Bot.* 51, 659-668). As the measurement is nondestructive, rapid and convenient, chlorophyll fluorescence method has many advantages in the quantification of stress effects on photosynthesis (Krause and Weis 1991, *Annu. Rev. Plant Physiol. Plant Mol. Biol.* 42, 313-349). Based on pulse amplitude modulation (PAM) and the saturation pulse method (Schreiber et al. 1986, *Photosynth. Res.* 10, 51-62), chlorophyll fluorescence yield provides quantitative information not only on steady-state photosynthesis, but also on various mechanisms of protection against stress-induced damage by excess radiation (Govindjee 1995, *Aust. J. Plant Physiol.* 22, 131-160; Demmig-Adams and Adams 1996, *Trends Plant Sci.* 1, 21-26; Kramer and Crofts 1996 *Photosynth. Environ.* 5, 25-66; Meng et al. 2001, *New Phytol.* 151, 585-595).

Dayan and Zaccaro (Pesticide Biochemistry and Physiology 2012, 103, 189-197) have developed a three-step assay to test selected herbicides and to determine whether induced chlorophyll fluorescence is a suitable marker to identify certain herbicide modes of action.

SUMMARY OF THE INVENTION

Thus, in a first aspect, the present invention refers to a method for identifying a polynucleotide encoding a polypeptide which confers herbicide tolerance to a plant as compared to a control plant, the method comprising
a. introducing and expressing in a plant a candidate polynucleotide encoding a candidate polypeptide,
b. retrieving plant material samples of the transformed plant of a. and plant material samples of a control plant
c. contacting the samples of b. with a herbicide,
d. incubating the samples of c. in darkness
e. exposing the samples of d. to light
and
f. measuring the photosynthetic quantum yield based on chlorophyll fluorescence, wherein an increase in the photosynthetic electron rate of the samples of the transformed plant as compared to the sample of the control plant is indicative for a herbicide tolerance conferring activity of said candidate polypeptide.

In a preferred embodiment, the introducing of the candidate polynucleotide occurs via *Agrobacterium*-mediated transformation.

In another preferred embodiment, candidate polynucleotide is expressed transiently (e.g. via PEG mediated transformation).

In another preferred embodiment, the plant material consists of plants, cut flowers, leaf material, fruits, berries, vegetables, flowers, flower organs, roots, tissue culture, seeds, bulbs, algae, mosses and tubers of plants.

In another preferred embodiment, the light [electromagnetic radiation] used for irradiating the samples is generated by a lamp, laser, or LED lamp.

In another preferred embodiment, the light [electromagnetic radiation] used for irradiating the samples has a wavelength of between 200 and 800 nm In another preferred embodiment, the light [electromagnetic radiation] used for irradiating the samples has an intensity of 10 to 1250 µmol/m$^2$/sec, a pulse duration of 0.001 to 1 seconds and an interval between the pulses of approximately 20 seconds.

In another preferred embodiment, the induced fluorescence originating from the plant material samples is measured between 600 and 800 nm In another preferred embodiment, the fluorescence radiation originating from the plant material samples is measured with an electronic camera selected from the group consisting of a video camera, CCD camera, line scan camera, photodiodes and photomultipliers.

In another embodiment, the present invention refers to a polynucleotide encoding a polypeptide which confers tolerance to a herbicide, said polynucleotide being identifiable by the method of the present invention.

KEY TO SEQUENCE LISTING

DETAILED DESCRIPTION OF PREFERRED EMBODIMENTS

Figure 1:
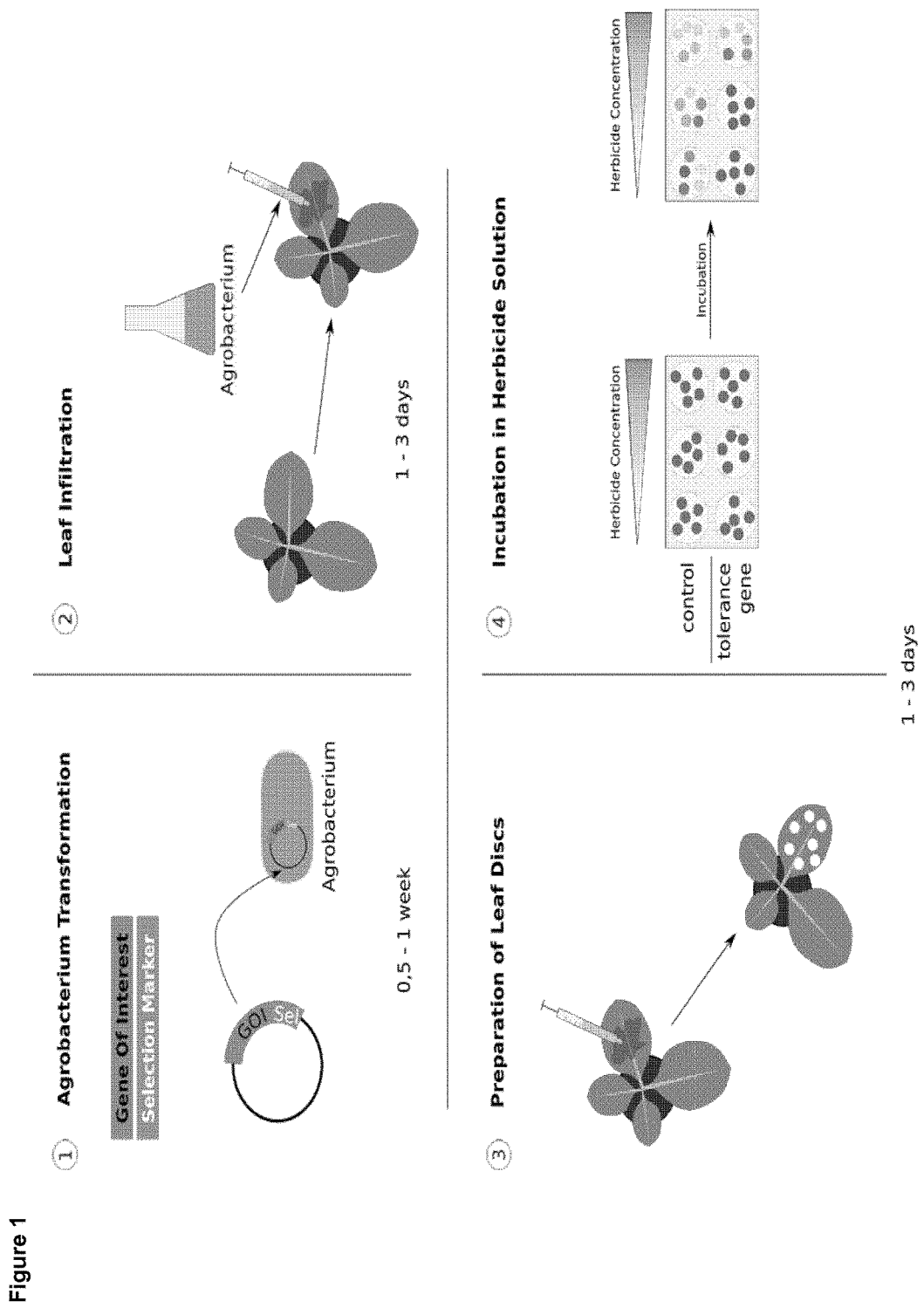
FIG. 1 shows a workflow to screen candidate genes for herbicide tolerance.
Figure 2:
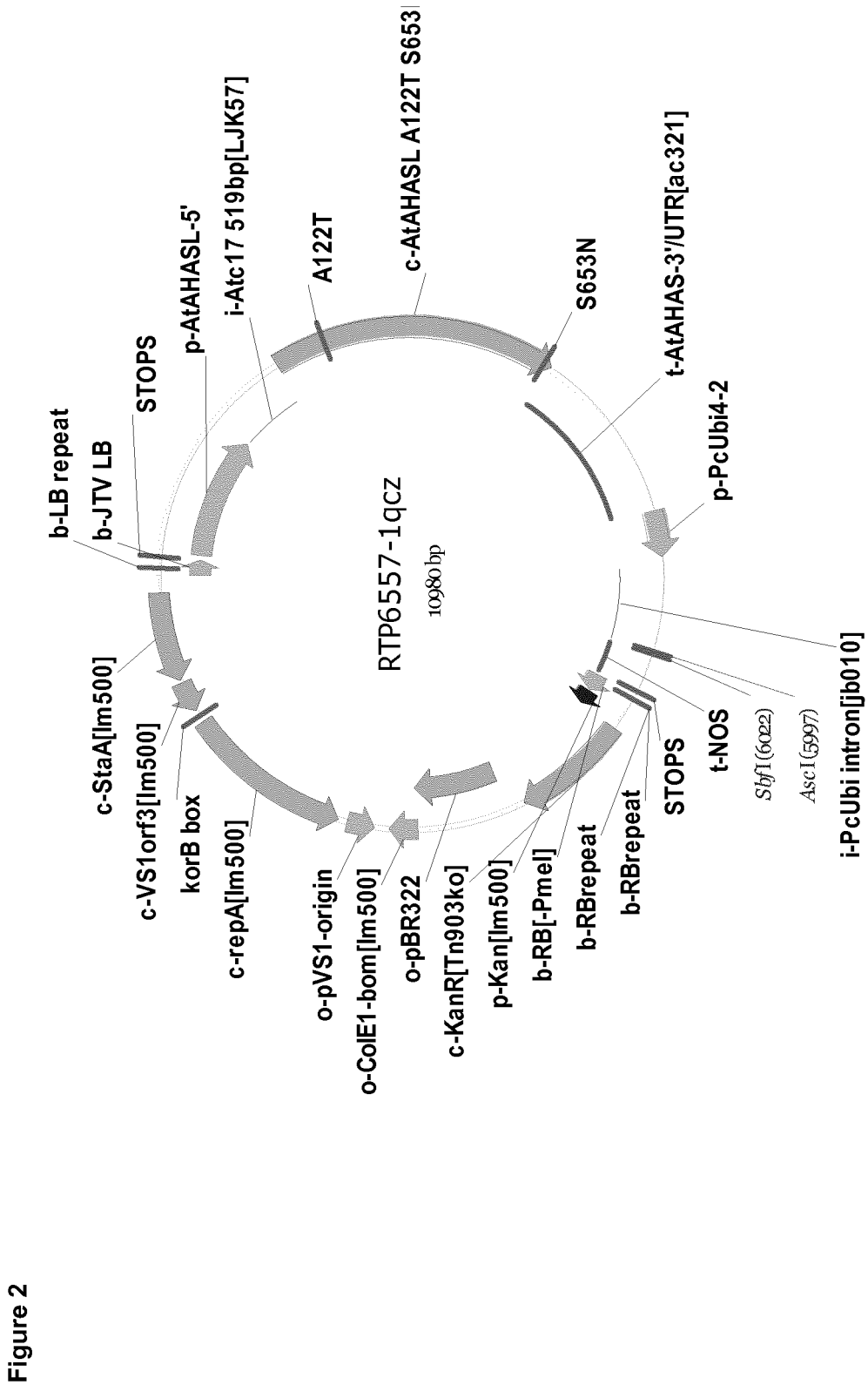
FIG. 2 shows vector map of binary vector used for transient transformation (SEQ ID NO: 11).

Thus, in a first aspect, the present invention refers to a method for identifying a polynucleotide encoding a polypeptide which confers herbicide tolerance to a plant as compared to a control plant, the method comprising a. introducing and expressing in a plant a candidate polynucleotide encoding a candidate polypeptide,
b. retrieving plant material samples of the transformed plant of a. and plant material samples of a control plant
c. contacting the samples of b. with a herbicide,
d. incubating the samples of c. in darkness
e. exposing the samples of d. to light
and
f. measuring the photosynthetic quantum yield wherein an increase in the photosynthetic electron rate of the samples of the transformed plant as compared to the sample of the control plant is indicative for a herbicide tolerance conferring activity of said candidate polypeptide.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms "gene(s)", "polynucleotide", "nucleic acid sequence", "nucleotide sequence", or "nucleic acid molecule(s)" as used herein include known types of modifications, for example, methylation, "caps", substitutions of one or more of the naturally occurring nucleotides with an analogue. Preferably, the DNA or RNA sequence comprises a coding sequence encoding the herein defined polypeptide.

As also used herein, the terms "nucleic acid" and "nucleic acid molecule" are intended to include DNA molecules (e.g. cDNA or genomic DNA) and RNA molecules (e.g. mRNA) and analogs of the DNA or RNA generated using nucleotide analogs. The nucleic acid molecule can be single-stranded or double-stranded.

"Polypeptide" refers to a polymer of amino acid (amino acid sequence) and does not refer to a specific length of the molecule. Thus, peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as

| Name | Organism | Nucleic acid | Amino acid |
|---|---|---|---|
| Cytochrome P450 monooxygenase | *Zea mays* | SEQ ID No: 1 | SEQ ID NO: 2 |
| Transketolase | *Spinacia oleracea* | SEQ ID No: 3 | SEQ ID NO: 4 |
| PPO_L379Q_F420M | *Amaranthus tuberculatus* | SEQ ID No: 5 | SEQ ID NO: 6 |
| PPO_R128L | *Amaranthus tuberculatus* | SEQ ID No: 7 | SEQ ID NO: 8 |
| PPO wildtype | *Alopecurus myosuroides* | SEQ ID No: 9 | SEQ ID NO: 10 |
| Cloning vector | | SEQ ID NO: 11 | | well as other modifications known in the art, both naturally occurring and non-naturally occurring. An "isolated" polynucleotide or nucleic acid molecule is separated from other polynucleotides or nucleic acid molecules, which are present in the natural source of the nucleic acid molecule. An isolated and/or a recombinant nucleic acid molecule may be a chromosomal fragment of several kb, or preferably, a molecule only comprising the coding region of the gene. Accordingly, an isolated and/or a recombinant nucleic acid molecule of the invention may comprise chromosomal regions, which are adjacent 5' and 3' or further adjacent chromosomal regions, but preferably comprises no such sequences which naturally flank the nucleic acid molecule sequence in the genomic or chromosomal context in the organism from which the nucleic acid molecule originates (for example sequences which are adjacent to the regions encoding the 5'- and 3'-UTRs of the nucleic acid molecule). An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of a protein in which the polypeptide is separated from some of the cellular components of the cells in which it is naturally or recombinantly produced.

The term "herbicide tolerance or resistance" as used herein it is intended that a plant that is tolerant or resistant to at least one herbicide at a level that would normally kill, or inhibit the growth of, a normal or wild-type plant.

Any increase in herbicide tolerance or resistance is an improved herbicide tolerance or resistance in accordance with the invention. For example, the improvement in herbicide tolerance or resistance can comprise a 1.5×, 2×, 2.5×, 3×, 5×, 10×, 20×, 30×, 40×, 50×, 75×, 100×, 150×, 200× or greater increase in any measurable parameter.

Generally, the term "herbicide" is used herein to mean an active ingredient that kills, controls or otherwise adversely modifies the growth of plants. More specifically, the term "herbicide" is meant to include any molecule that, when exogenously applied to a plant, has a deleterious effect on said plant. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by the herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By "herbicide-tolerant" or "herbicide-resistant" plant, it is intended that a plant that is tolerant or resistant to at least one herbicide at a level that would normally kill, or inhibit the growth of, a normal or wild-type plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

As used herein, "plant" is meant to include not only a whole plant but also a part thereof i.e., one or more cells, and tissues, including for example, leaves, stems, shoots, roots, flowers, fruits and seeds.

In principle all plants, and parts thereof, can be used as host organism. Preferred transgenic plants are, for example, selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Cari-folaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants such as plants advantageously selected from the group of the genus peanut, oilseed rape, canola, sunflower, safflower, olive, sesame, hazelnut, almond, avocado, bay, pumpkin/squash, linseed, soya, pistachio, borage, maize, wheat, rye, oats, sorghum and millet, triticale, rice, barley, cassava, potato, sugarbeet, egg plant, alfalfa, and perennial grasses and forage plants, oil palm, vegetables (brassicas, root vegetables, tuber vegetables, pod vegetables, fruiting vegetables, onion vegetables, leafy vegetables and stem vegetables), buckwheat, Jerusalem artichoke, broad bean, vetches, lentil, dwarf bean, lupin, clover and Lucerne for mentioning only some of them.

The terms "wild type", "control" or "reference" are exchangeable and can be a cell or a part of organisms such as an organelle like a chloroplast or a tissue, or an organism, in particular a plant, which was not modified or treated according to the herein described process according to the invention. Accordingly, the cell or a part of organisms such as an organelle like a chloroplast or a tissue, or an organism, in particular a plant used as wild type, control or reference corresponds to the cell, organism, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property. Preferably, any comparison is carried out under analogous conditions. The term "analogous conditions" means that all conditions such as, for example, culture or growing conditions, soil, nutrient, water content of the soil, temperature, humidity or surrounding air or soil, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-"-organelle, -cell, -tissue or -organism, in particular plant, relates to an organelle, cell, tissue or organism, in particular plant, which is nearly genetically identical to the organelle, cell, tissue or organism, in particular plant, of the present invention or a part thereof preferably 90% or more, e.g. 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a subject, e.g. an organelle, a cell, a tissue, an organism, in particular a plant, which is genetically identical to the organism, in particular plant, cell, a tissue or organelle used according to the process of the invention except that the responsible or activity conferring nucleic acid molecules or the gene product encoded by them are amended, manipulated, exchanged or introduced according to the inventive process. In case, a control, reference or wild type differing from the subject of the present invention only by not being subject of the process of the invention can not be provided, a control, reference or wild type can be an organism in which the cause for the modulation of an activity conferring the enhanced tolerance or resistance to herbicides as compared to a corresponding, e.g. non-transformed, wild type plant cell, plant or part thereof or expression of the nucleic acid molecule of the invention as described herein has been switched back or off, e.g. by knocking out the expression of responsible gene product, e.g. by antisense or RNAi or miRNA inhibition, by inactivation of an activator or agonist, by activation of an inhibitor or antagonist, by inhibition through adding inhibitory antibodies, by adding active compounds as e.g. hormones, by introducing negative dominant mutants, etc. A gene production can for example be knocked out by introducing inactivating point mutations, which lead to an enzymatic activity inhibition or a destabilization or an inhibition of the ability to bind to cofactors etc. Accordingly, preferred reference subject is the starting subject of the present process of the invention. Preferably, the reference and the subject matter of the invention are compared after standardization and normalization, e.g. to the amount of total RNA, DNA, or protein or activity or expression of reference genes, like housekeeping genes, such as ubiquitin, actin or ribosomal proteins.

The introduction of the polynucleotides according to the invention, into plants, can in principle be done by all of the methods known to those skilled in the art. The introduction of the nucleic acid sequences gives rise to recombinant or transgenic organisms.

The transfer of foreign genes into the genome of a plant is called transformation. Generally, "transformation" is defined as a process for introducing heterologous DNA into a plant cell, plant tissue, or plant. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time. Transformed plant cells, plant tissue, or plants are understood to encompass not only the end product of a transformation process, but also transgenic progeny thereof.

Well-known methods described for the transformation and regeneration of plants from plant tissues or plant cells can be utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in Jenes B. et al., Techniques for Gene Transfer, in: Transgenic Plants, Vol. 1, Engineering and Utilization, eds. Kung S. D and Wu R., Academic Press (1993) 128-143 and in Potrykus, Annu. Rev. Plant Physiol. Plant Molec. Biol. 42, 205 (1991). The nucleic acids or the construct to be expressed is preferably cloned into a vector which is suitable for transforming *Agrobacterium tumefaciens*, for example pBin19 (Bevan et al., Nucl. Acids Res. 12, 8711 (1984)). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. 16, 9877 (1988) or is known inter alia from White F. F., Vectors for Gene Transfer in Higher Plants; in Transgenic Plants, Vol. 1, Engineering and Utilization, eds. Kung S. D. and Wu R., Academic Press, 1993, pp. 15-38.

Agrobacteria transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassava, arrowroot, tagetes, alfalfa, lettuce and the various tree, nut and vine species, in particular oil-containing crop plants such as soybean, peanut, castor oil plant, sunflower, corn, cotton, flax, oilseed rape, coconut, oil palm, safflower (*Carthamus tinctorius*) or cocoa bean, or in particular corn, wheat, soybean, rice, cotton and canola, e.g. by bathing bruised leaves or chopped leaves in an agrobacterial solution and then culturing them in suitable media.

Thus, in a preferred embodiment, the introducing of the candidate polynucleotide occurs via *Agrobacterium*-mediated transformation.

The term "expression" refers to the transcription and/or translation of a codogenic gene segment or gene. As a rule, the resulting product is an mRNA or a protein.

The expression of the candidate polynucleotide according to this invention can be constitutive, e.g. due to a stable permanent transgenic expression or to a stable mutation in the corresponding endogenous gene encoding the nucleic acid molecule of the invention or to a modulation of the expression or of the behavior of a gene conferring the expression of the polypeptide of the invention, or transient, e.g. due to an transient transformation or temporary addition of a modulator such as a agonist or antagonist or inducible, e.g. after transformation with a inducible construct carrying the nucleic acid molecule of the invention under control of a inducible promoter and adding the inducer, e.g. tetracycline or as described herein below.

In a particularly preferred embodiment, the candidate polynucleotide is expressed transiently.

In principle, any material of a plant can be retrieved to be analyzed for the activity of a candidate polypeptide. Preferably, the plant material consists of plants, cut flowers, leaf material, fruits, berries, vegetables, flowers, flower organs, roots, tissue culture, seeds, bulbs, algae, mosses and tubers of plants. In a particularly preferred embodiment, the plant material is leaf material.

Usually, plant material is retrieved by excising suitable material with suitable excising instruments known to the person skilled in the art. Leaf discs are punched out by methods known the skilled artisan and placed into incubation plates containing suitable buffers for contacting with a herbicide according to step c. of the method of the present invention. This contacting and subsequent incubation of the leaf discs with the test herbicide can take several hours up to several days.

Upon contacting the samples with the test herbicide, the samples are incubated in a growth chamber at 22° C., 75% relative humidity and 110 µmol Phot*$m^{-2}$*$s^{-1}$ with 14:10 h light:dark photoperiod. Typical incubation times include 24 to 72 hrs in the dark, preferably 48 h In a next step according to the method of the present invention the samples are analyzed with the PAM imaging system for their PSII yield according to manufacturer's instruction.

In one embodiment, the light used for irradiating the samples is generated by a lamp, laser, or LED lamp.

In a preferred embodiment, the light used for irradiating the samples has a wavelength of between 200 and 800 nm.

In another preferred embodiment, the light [electromagnetic radiation] used for irradiating the samples has an intensity of 10 to 1250 µmol/$m^2$/sec, a pulse duration of 0.001 to 1 seconds and an interval between the pulses of approximately 20 seconds.

In a next step according to the method of the present invention, the photosynthetic quantum yield in the samples (transformed and control) is measured.

The quantum yield of photosynthesis is a definitive measure of the energetic efficiency of photoautotrophy. The quantum yield for any defined light-dependent process is the rate at which that defined event occurs relative to the rate of photon absorption by the system (J. Skillman, J. Exp. Bot. (2008) 59 (7): 1647-1661). As such, the quantum yield is a measure of the efficiency with which absorbed light produces a particular effect in a plant exposed to distinct conditions.

Generally, the fluorescence radiation originating from the plant material samples is measured with an electronic camera selected from the group consisting of a video camera, CCD camera, line scan camera, photodiodes and photomultipliers.

A wide spectrum of PAM chlorophyll fluorometers is available for non-intrusive assessment of photosynthesis from single cells to whole leaves. All of these instruments employ the so-called "Pulse-Amplitude-Modulation" (PAM) measuring principle, which is unique in providing a selective measure of the relative chlorophyll fluorescence quantum yield. With the help of the "Saturation Pulse Method", the quantum yield of photosynthetic energy conversion is derived (see for detailed information http://www.walz.com/products/categories.html).

In a preferred embodiment, the induced fluorescence originating from the plant material samples is measured between 600 and 800 nm.

The "photosynthesis electron transport rate" is known the person skilled in the art as a relative measure of photosynthesis. Stress conditions, such as exposure to herbicides, interfere with the plant's photosynthesis electron transport system. Thus, an alteration of the normal electron flow rate caused by internal or external stresses like treatment with herbicides can be measured by monitoring chlorophyll fluorescence.

Consequently, the increase in photosynthetic yield (psiI yield) of the samples of the transformed plant as compared to the sample of the control plant is indicative for a herbicide tolerance conferring activity of said candidate polypeptide.

In another embodiment, the present invention refers to a polynucleotide encoding a polypeptide which confers tolerance to a herbicide, said polynucleotide being identifiable by the method of the present invention.

EXAMPLES

Example 1: Cloning of Gene of Interest and *Agrobacterium* Transformation

Open reading frames of gene of interests (GOI; SEQ ID NOs: 1, 3, 5, 7, or 9) were synthesized by standard gene synthesis technologies (Life Technologies GmbH, Darmstadt, Germany). The genes were synthesized as native sequences or as codon optimized versions adapted to the codon usage for tobacco, *Arabidopsis* or *Glycine max*. Gene sequences were cloned in a binary vector (FIG. 1, SEQ ID NO:11) for *Agrobacterium* mediated transformation via AscI and SbfI restriction sites with standard cloning techniques as described in Sambrook et al. (Molecular cloning (2001) Cold Spring Harbor Laboratory Press) The binary vector for transformation contained the GOI in between a parsley ubiquitin promoter (PcUbi) and the nopaline synthase terminator (NOS) sequence. Binary plasmids are introduced to *Agrobacterium tumefaciens* strain (GV2260) with standard transformation procedures as described in Weigel and Glazebrook (*Arabidopsis*—A Laboratory Manual, (2002) Cold Spring Habor Laboratory Press).

Example 2: Transient Protein Expression in Tobacco Leafs

Transient expression of GENE-OF-INTEREST (GOI) (e.g. SEQ ID NOs: 1, 3, 5, 7, or 9) were done as described previously (Voinnet O., et al., 2003, The Plant Journal 33, 949-956). In brief, cloning of GOI and *Agrobacterium* transformation (strain: GV2260) were done as described in EXAMPLE 1. Young leaves of *Nicotiana benthamiana* were infiltrated with transgenic *Agrobacterium* suspension ($OD^{600}$ of 1.0) harboring binary vector constructs containing a GOI gene controlled by a promoter and terminator sequence. 48 h to 72 h after infiltration punches of leave discs (0.75 cm in diameter) were transferred to 6-well plates with medium (half strength Linsmaier-Skoog (Linsmaier and Skoog (1965) Physiol. Plant. 18: 100-127) nutrient solution or water) containing herbicide of interest in different concentrations. Multi well plates were incubated in a growth chamber at 22° C., 75% relative humidity and 110 µmol Phot*$m^{-2}$*$s^{-1}$ with 14:10 h light:dark photoperiod.

Figure 3:
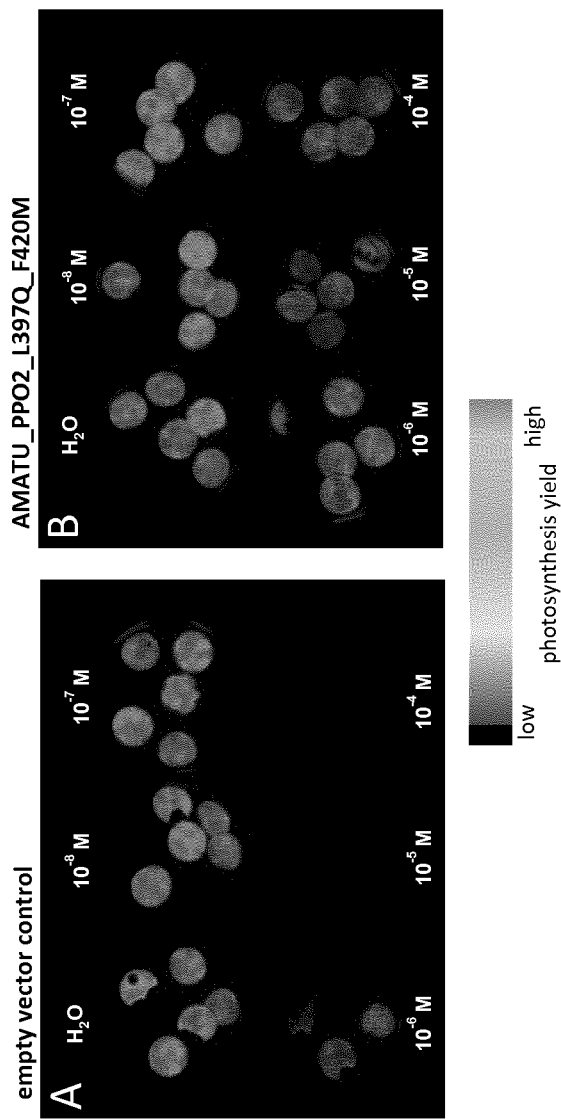
FIG. 3 shows the visualization of photosynthetic yield with PAM imaging system. Photosynthetic yield of leaf discs transformed with an empty vector control and treated with different herbicide concentrations shown on panel A. Panel B shows photosynthetic yield of leaf discs transformed with a nucleic acid encoding a mutated protoporphyrinogen oxidase (PPO) (nucleic acid SEQ ID NO: 5; amino acid SEQ ID NO:6) and treated with different herbicide concentrations.

Example 3: Demonstration of Herbicide Tolerance of Transiently Transformed Tobacco Leaf Discs Leaf discs, generated as described in EXAMPLE 2, expressing a protein encoded by GOI, were subjected to analysis on improved tolerance to herbicide treatment. For analysis of herbicide damage, chlorophyll fluorescence were identified as indicative marker (Dayan and Zaccaro (2012) Pest. Biochem. Physiol. 102: 189-197). In addition to monitor herbicide effect by visual inspection the photosynthetic yield of photosystem II were done with a MAXI imaging PAM machine (IMAGINE-PAM M-Series, Walz, Effeltrich, Germany) 24 h, 48 h and 96 h after starting herbicide treatment (FIG. 3). PSII yield were measured as per manufacturer instructions. Tolerance factors were calculated based on IC50 values of PSII yield inhibition of transformed versus empty vector-transformed leaf discs.

| Enzyme | Sequence origin | Mutant | Herbicide | Tolerance factor |
|---|---|---|---|---|
| Cytochrome P450 | *Zea mays* | wildtype | Bentazon | 13.4 |
| Transketolase | *Spinacia oleracea* | wildtype | Cornexistin | 3.6 |
| Protoporphyrinogen IX Oxidase (PPO) | *Amaranthus tuberculatus* | L397Q_F420M | Saflufenacil | 150 |
| Protoporphyrinogen IX Oxidase (PPO) | *Amaranthus tuberculatus* | R128L | Saflufenacil | 170 |
| Protoporphyrinogen IX Oxidase (PPO) | *Amaranthus tuberculatus* | R128L | BAS 850H | 28.7 |
| Protoporphyrinogen IX Oxidase (PPO) | *Alopecurus myosuroides* | wildtype | Saflufenacil | 177 |

The invention claimed is:

1. A method for identifying a polynucleotide encoding a polypeptide which confers herbicide tolerance to a plant as compared to a control plant, the method comprising
   a. introducing and expressing in a plant a candidate polynucleotide encoding a candidate polypeptide, wherein the candidate polynucleotide is expressed transiently,
   b. retrieving plant material samples of the transformed plant of a. and plant material samples of a control plant
   c. contacting the samples of b. with a herbicide,
   d. incubating the samples of c. in darkness
   e. exposing the samples of d. to light
   and
   f. measuring the photosynthetic quantum yield
   wherein an increase in the electron transport rate of the samples of the transformed plant as compared to the sample of the control plant is indicative for a herbicide tolerance conferring activity of said candidate polypeptide.

2. The method according to claim 1, wherein the introducing of the candidate polynucleotide occurs via *Agrobacterium*-mediated transformation.

3. The method according to claim 1, wherein the plant material consists of plants, cut flowers, leaf material, fruits, berries, vegetables, flowers, flower organs, roots, tissue culture, seeds, bulbs, algae, mosses, or tubers of plants.

4. The method according to claim 1, wherein the light used for irradiating the samples is generated by a lamp, laser, or LED lamp.

5. The method according to claim 1, wherein the light used for irradiating the samples has a wavelength of between 200 and 800 nm.

6. The method according to claim 1, wherein the light used for irradiating the samples has an intensity of 10 to 1250 µmol/m2/sec, a pulse duration of 0.001 to 1 seconds and an interval between the pulses of approximately 20 seconds.

7. The method according to claim 1, wherein the induced fluorescence originating from the plant material samples is measured between 600 and 800 nm.

8. The method according to claim 1, wherein the fluorescence radiation originating from the plant material samples is measured with a video camera, CCD camera, line scan camera, photodiode, or photomultiplier.

* * * * *